(12) United States Patent
Neumann

(10) Patent No.: US 11,823,785 B2
(45) Date of Patent: Nov. 21, 2023

(54) METHODS AND SYSTEMS FOR CALCULATING NUTRITIONAL REQUIREMENTS IN A DISPLAY INTERFACE

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 46 days.

(21) Appl. No.: 16/919,532

(22) Filed: Jul. 2, 2020

(65) Prior Publication Data
US 2022/0005578 A1    Jan. 6, 2022

(51) Int. Cl.
*G16H 20/60* (2018.01)
*G06N 20/00* (2019.01)
*G06F 16/248* (2019.01)
*G06F 16/242* (2019.01)

(52) U.S. Cl.
CPC ........... *G16H 20/60* (2018.01); *G06F 16/248* (2019.01); *G06F 16/2428* (2019.01); *G06N 20/00* (2019.01)

(58) Field of Classification Search
CPC ... G16H 20/60; G06F 16/2428; G06F 16/248; G06N 20/00
See application file for complete search history.

(56) References Cited

U.S. PATENT DOCUMENTS

| | | | |
|---|---|---|---|
| 6,980,999 B1 | 12/2005 | Grana | |
| 8,920,175 B2 | 12/2014 | Black et al. | |
| 8,924,239 B1 * | 12/2014 | Kurple | G16H 20/60 705/2 |
| 9,011,153 B2 * | 4/2015 | Bennett | G16H 20/60 434/127 |
| 10,360,495 B2 | 7/2019 | Chapela et al. | |
| 2006/0004762 A1 * | 1/2006 | Berning | G16H 10/60 |

(Continued)

FOREIGN PATENT DOCUMENTS

| WO | WO2016065463 | 5/2016 | |
|---|---|---|---|
| WO | WO-2016065463 A1 * | 5/2016 | ............... A61B 5/00 |

(Continued)

OTHER PUBLICATIONS https://www.ncbi.nlm.nih.gov/pmc/articles/PMC5579706/pdf/nutrients-09-00913.pdf.

(Continued)

*Primary Examiner* — Sheetal R Paulson
(74) *Attorney, Agent, or Firm* — CALDWELL INTELLECTUAL PROPERTY LAW

(57) ABSTRACT

A system for calculating nutritional requirements in a display interface the system including a computing device configured to initiate a display interface within the computing device; retrieve an input, including an input credential, and wherein the input relates a representative profile to a nutritional requirement; generate a training set using the input; receive a meal option; calculate using a machine-learning process, a nutritional requirement of the meal option using the training set; determine the nutritional requirement of the meal option as a function of the machine-learning process; and display the nutritional requirement within the display interface.

20 Claims, 8 Drawing Sheets

(56) References Cited

U.S. PATENT DOCUMENTS

| | | | |
|---|---|---|---|
| 2013/0280681 A1* | 10/2013 | Narayan | G16H 20/60 434/127 |
| 2014/0207914 A1* | 7/2014 | Robinson | G06Q 10/10 709/219 |
| 2014/0255882 A1 | 9/2014 | Hadad et al. | |
| 2015/0161910 A1 | 6/2015 | Bailor | |
| 2016/0364548 A1 | 12/2016 | Springer | |
| 2017/0061551 A1* | 3/2017 | Olayanju | G06Q 50/01 |
| 2018/0144820 A1* | 5/2018 | Grimmer | G16H 20/60 |
| 2018/0233064 A1 | 8/2018 | Dunn et al. | |
| 2018/0293638 A1 | 10/2018 | Simpson | |
| 2019/0252058 A1* | 8/2019 | Wolf | G09B 19/0092 |
| 2019/0304000 A1* | 10/2019 | Simpson | G01N 33/492 |
| 2019/0371452 A1* | 12/2019 | Mainardi | G16H 20/60 |
| 2020/0233875 A1* | 7/2020 | Penev | G16H 20/60 |
| 2021/0118545 A1* | 4/2021 | Sathyanarayana | G06N 20/20 |

FOREIGN PATENT DOCUMENTS

| | | | |
|---|---|---|---|
| WO | WO2020115362 | 6/2020 | |
| WO | WO-2021219528 A1 * | 11/2021 | G16H 20/60 |

OTHER PUBLICATIONS https://www.researchgate.net/ publication/334529528_A_food_recommender_system_considering_nutritional_information_and_user_preferences (via 'Download full-text PDF' link).
https://www.researchgate.net/profile/Luis_Rita2/publication/340133854_Machine_Learning_for_Building_a_Food_Recommendation_System/links/5e7aa059a6fdcc57b7bbaf10/Machine-Learning-for-Building-a-Food-Recommendation-System.pdf.

* cited by examiner

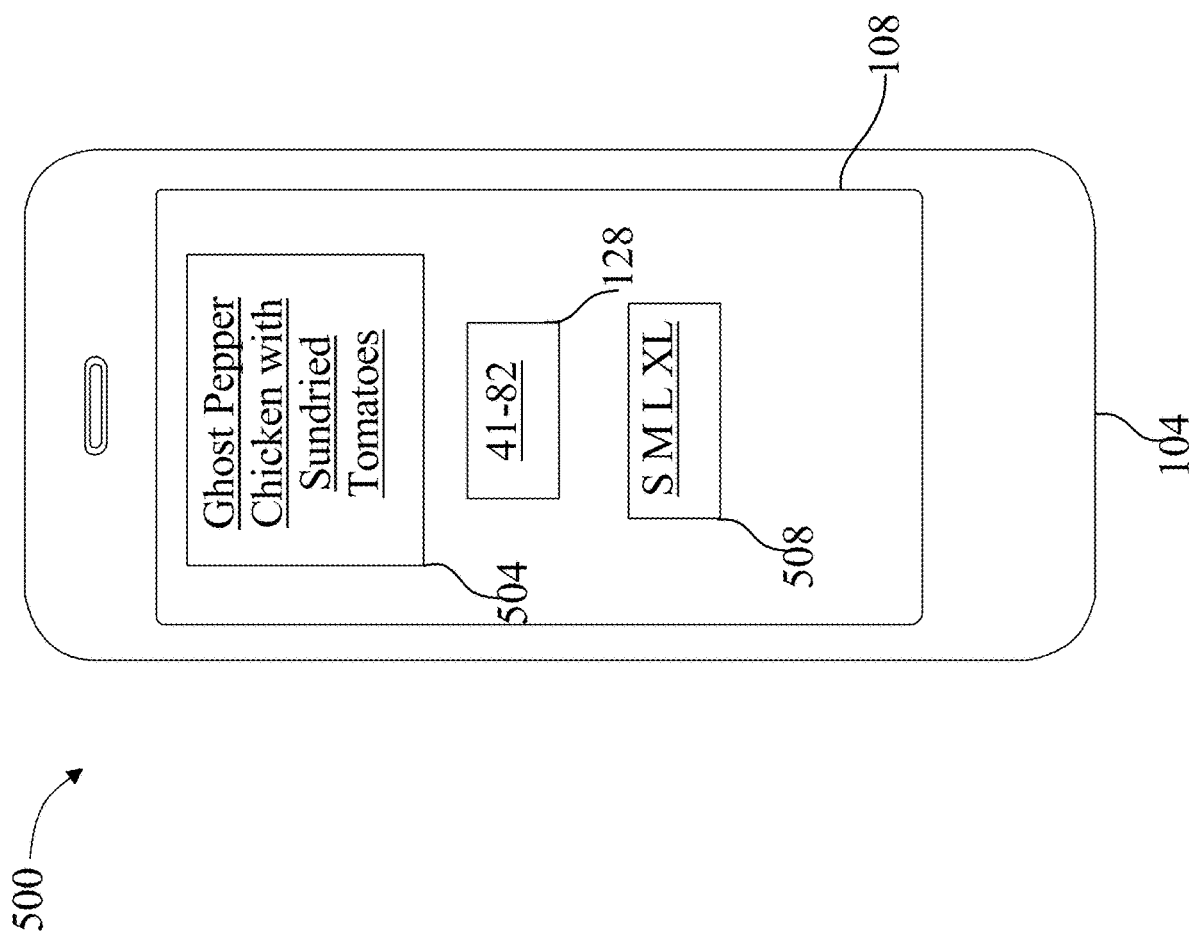

METHODS AND SYSTEMS FOR CALCULATING NUTRITIONAL REQUIREMENTS IN A DISPLAY INTERFACE

FIELD OF THE INVENTION

The present invention generally relates to the field of nourishment. In particular, the present invention is directed to methods and systems for calculating nutritional requirements in a display interface.

BACKGROUND

Informed selection of meal options can be challenging. Frequently, one is overrun with numerous decisions. Informed selection can aid in a beneficial response.

SUMMARY OF THE DISCLOSURE

In an aspect, a system for calculating nutritional requirements in a display interface the system comprising a computing device configured to initiate a display interface within the computing device; retrieve an input, including an input credential, and wherein the input relates a representative profile to a nutritional requirement; generate a training set using the input; receive a meal option; calculate using a machine-learning process, a nutritional requirement of the meal option using the training set; determine the nutritional requirement of the meal option as a function of the machine-learning process; and display the nutritional requirement within the display interface.

In an aspect, a method of calculating nutritional requirements in a display interface the method comprising initiating by a computing device, a display interface within the computing device; retrieving by the computing device, an input, including an input credential, and wherein the input relates a representative profile to a nutritional requirement; generating by the computing device, a training set using the input; receiving by the computing device, a meal option; calculating by the computing device, using a machine-learning process, a nutritional requirement of the meal option using the training set; determining by the computing device, the nutritional requirement of the meal option as a function of the machine-learning process; and displaying by the computing device, the nutritional requirement within the display interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 5A-5B are diagrammatic representations of display interface;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for calculating nutritional requirements in a display interface. In an embodiment, an input relating a representative profile to a nutritional requirement is utilized to generate a training set, and calculating using a machine-learning process, a nutritional requirement of a meal option. A calculated nutritional requirement is displayed within a display interface.

Figure 1:
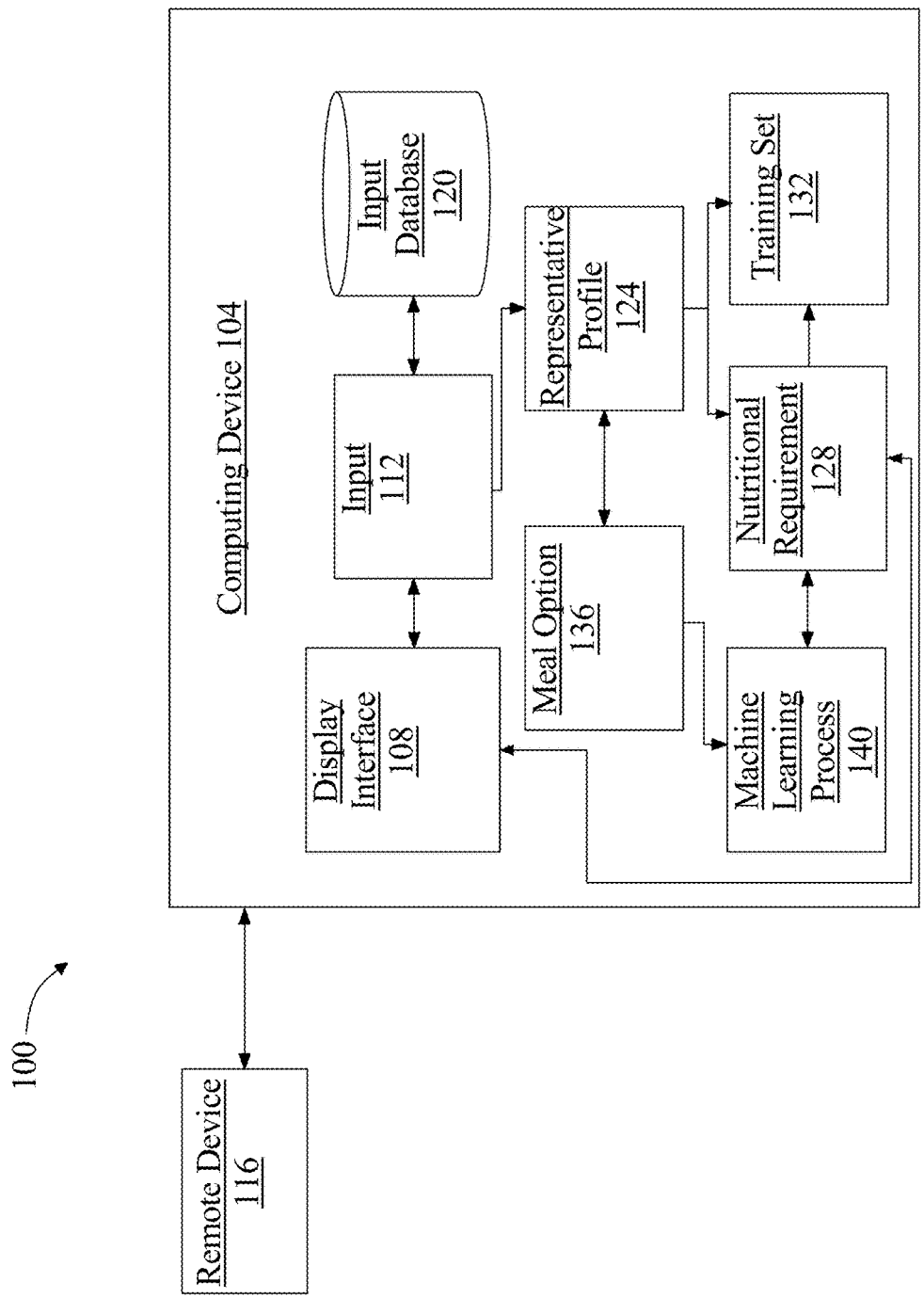
FIG. 1 is a block diagram illustrating an exemplary embodiment of a system for calculating nutritional requirements in a display interface.

Referring now to FIG. 1, an exemplary embodiment of a system 100 for calculating nutritional requirements in a display interface is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or connect with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or connect with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an association, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be transmitted to and/or from a computer and/or a computing device 104. Computing device 104 may include but is not limited to, for example, a computing device 104 or cluster of computing devices 104 in a first position and a second computing device 104 or cluster of computing devices 104 in a second position. Computing device 104 may include one or more computing devices 104 dedicated to data storage, security, dispersal of traffic for load balancing, and the like. Computing device 104 may distribute one or more computing tasks as described below across a plurality of computing devices 104 of computing device 104, which may operate in parallel, in series, redundantly, or in any other manner used for dispersal of tasks or memory between computing devices 104. Computing device 104 may be implemented using a "shared nothing" architecture in which data is cached at the operative, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence recurrently until a desired or commanded outcome is achieved; repetition of a step or a sequence of steps may be performed iteratively and/or recursively using outputs of previous repetitions as inputs to subsequent repetitions, assembling inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to initiate a display interface within computing device 104. A "display interface," as used in this disclosure, is a user interface that allows a user to interface with computing device 104 through graphical icons, audio indicators, command labels, text navigation and the like. Display interface 108 may include a form or other graphical element having display fields, where one or more elements of information may be displayed. Display interface 108 may include slides or other user commands that may allow a user to select one or more characters. Display interface 108 may include free form textual entries, where a user may type in responses and/or messages. Display interface 108 may display data output fields including text, images, or the like. Display interface 108 may include data input fields such as text entry windows, drop-down lists, buttons, checkboxes, radio buttons, sliders, links, or any other data input interface that may capture user interaction as may occur to persons skilled in the art upon reviewing the entirety of this disclosure. Display interface 108 may be provided, without limitation, using a web browser, a native application, a mobile application, or the like.

With continued reference to FIG. 1, computing device 104 is configured to retrieve an input, including an input credential, relating a representative profile to a nutritional requirement. An "input," as used in this disclosure, is any entry including without limitation articles, journals, scientific observations, scientific discoveries, medical observations, expert knowledge, books, articles, blog posts, medical guidelines, scientific guidelines, observational studies, randomized control studies, quantitative research, qualitative research, descriptive research, explanatory research, best practices, evidence based research, and the like. An input 112 may be obtained from one or more experts, including any person who has a comprehensive and authoritative knowledge or skill in a particular area. An input 112 includes an input credential, which identifies any qualification, achievement, quality, experience, and/or authority that indicates the author of an input is qualified to create a submission.

With continued reference to FIG. 1, an input may be received from a remote device. A "remote device," as used in this disclosure, is a computing device, including but not limited to a mobile device such as a smartphone, tablet, laptop, desktop, and the like. An input may be received by computing device 104 using any network methodology as described herein. Computing device 104 retrieves an input from input database 120. Input database 120 may be implemented without limitation, as a relational database, a key-value retrieval datastore such as a NOSQL database, or any other format or structure for use as a datastore that a person skilled in the art would recognize as suitable upon review of the entirety of this disclosure.

With continued reference to FIG. 1, an input 112 relates a representative profile to a nutritional requirement. A "representative profile," as used in this disclosure, is a conglomerate of one or more human profiles. A human profile, identifies one or more groups and/or classes of human beings based on one or more demographic factors, including but not limited to race, ethnic origin, physical body measurements, disease type, geographical location, season in geographical location, biological extraction, component of a biological extraction, physical situation such as perimenopause, childbirth, menopause, low testosterone, andropause, genetic condition and the like. A group of human beings may be identified based on a demographic factor that groups human beings based on what stage of life they are currently in. A stage of life may be based on stages of a human life cycle such as infancy, toddler years, childhood, puberty, older adolescence, adulthood, middle age, senior years, and the like. A group of human beings may be identified based on a demographic factor that groups human beings based on gender, including male or female. A group of human beings may be identified based on a demographic factor that groups human beings based on pre-determined income levels. A group of human beings may be identified based on a demographic factor that groups human beings based on highest educational level achieved. A group of human beings may be identified based on one or more demographic factors, such as chronological age and gender, or stage of life and gender. Information pertaining to a representative profile 124, and human profiles may be stored within input database 120. A representative profile 124 includes a demographic label. A "demographic label," as used in this disclosure, is an identifier of one or more demographic factors used to create a human profile. For instance and without limitation, a demographic label may identify a demographic factor such as age, that is used to create a human profile, consisting of humans within the age range of between 35 and 40 years old. In yet another non-limiting example, a demographic label may identify a two demographic factors used to create a human profile, consisting of humans who make an annual salary of between $120,000 and $200,000, and who are of the female sex. A representative profile 124, may be selected using a classifier. A "classifier," as used in this disclosure, is a machine-learning model, such as a mathematical model, neural net, or program generated by a machine learning algorithm known as a classification algorithm, that sorts inputs into categories or bins of data, outputting the categories or bins of data and/or labels associated therewith. In an embodiment, a classification algorithm may utilize an input credential as an input and output a representative profile. A classifier and/or a classification algorithm may be implemented, without limitation, as described in U.S. Nonprovisional application Ser. No. 16/727,113, filed on Dec. 29, 2019, and entitled "METHODS AND SYSTEMS FOR PHYSIOLOGICALLY INFORMED NETWORK SEARCHING," the entirety of which is incorporated herein by reference.

Continuing to refer to FIG. 1, computing device 104 is configured to input biological extraction 108 to an index classifier 112. In an embodiment, index classifier 112 is a classifier. A "classifier," as used in this disclosure is a machine-learning model, such as a mathematical model, neural net, or program generated by a machine learning algorithm known as a "classification algorithm 120," as described in further detail below, that sorts inputs into categories or bins of data, outputting the categories or bins of data and/or labels associated therewith. Index classifier 112 is a classifier configured to input biological extractions 108 and output web search indices 116 a-n, where outputting web search indices 116 a-n here signifies outputting labels of web search indices 116 a-n.

Still referring to FIG. 1, a "web search index," as defined in this disclosure is a data structure that stores uniform resource locators (URLs) of web pages together with one or more associated data that may be used to retrieve URLs by querying the web search index; associated data may include keywords identified in pages associated with URLs by programs such as web crawlers and/or "spiders." A web search index may include any data structure for ordered storage and retrieval of data, which may be implemented as a hardware or software module. A web search index may be implemented, without limitation, as a relational database, a key-value retrieval datastore such as a NOSQL database, or any other format or structure for use as a datastore that a person skilled in the art would recognize as suitable upon review of the entirety of this disclosure. Data entries in a web search index may be flagged with or linked to one or more additional elements of information, which may be reflected in data entry cells and/or in linked tables such as tables related by one or more indices 116 a-n in a relational database. Persons skilled in the art, upon reviewing the entirety of this disclosure, will be aware of various ways in which data entries in a web search index may reflect categories, cohorts, and/or populations of data consistently with this disclosure. In an embodiment, a web search query 140 at a search engine may be submitted as a query to a web search index, which may retrieve a list of URLs responsive to the query. In an embodiment, each web search index of plurality of web search indices 116 a-n may be identified by a user cohort label, which as used in this disclosure is a label that matches a set or cluster of users having similar physiological data and/or attributes. In an embodiment, index classifier 112 is generated by executing a classification algorithm 120 clustering a plurality of user physiological data records to a plurality of user cohort labels.

Computing device 104 and/or another device may generate index classifier 112 using a classification algorithm 120, defined as a processes whereby a computing device 104 derives a classifier from training data 124. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, training data 124, as used in this disclosure, is data containing correlations that a machine-learning process may use to model relationships between two or more categories of data elements. For instance, and without limitation, training data 124 may include a plurality of data entries, each entry representing a set of data elements that were recorded, received, and/or generated together; data elements may be correlated by shared existence in a given data entry, by proximity in a given data entry, or the like. Multiple data entries in training data 124 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 124 according to various correlations; correlations may indicate causative and/or predictive links between categories of data elements, which may be modeled as relationships such as mathematical relationships by machine-learning processes as described in further detail below. Training data 124 may be formatted and/or organized by categories of data elements, for instance by associating data elements with one or more descriptors corresponding to categories of data elements. As a non-limiting example, training data 124 may include data entered in standardized forms by persons or processes, such that entry of a given data element in a given field in a form may be mapped to one or more descriptors of categories. Elements in training data 124 may be linked to descriptors of categories by tags, tokens, or other data elements; for instance, and without limitation, training data 124 may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data 124 may include one or more elements that are not categorized; that is, training data 124 may not be formatted or contain descriptors for some elements of data. Machine-learning algorithms and/or other processes may sort training data 124 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 124 to be made applicable for two or more distinct machine-learning algorithms as described in further detail below. Training data 124 used by computing device 104 may correlate any input data as described in this disclosure to any output data as described in this disclosure.

Still referring to FIG. 1, index training data 124, defined as training data 124 used to generate index classifier 112, may include, without limitation, a plurality of data entries, each data entry including one or more elements of physiological data such as biological extractions 108, and one or more correlated user cohort labels, where user cohort labels and associated physiological profiles may be identified using feature learning algorithms 128 as described below. Index training data 124 and/or elements thereof may be added to, as a non-limiting example, by classification of multiple users' physiological data to cohort labels using one or more classification algorithms 120.

Still referring to FIG. 1, computing device 104 may be configured to generate index classifier 112 using a Naïve Bayes classification algorithm 120. Naïve Bayes classification algorithm 120 generates classifiers by assigning class labels to problem instances, represented as vectors of element values. Class labels are drawn from a finite set. Naïve Bayes classification algorithm 120 may include generating a family of algorithms that assume that the value of a particular element is independent of the value of any other element, given a class variable. Naïve Bayes classification algorithm 120 may be based on Bayes Theorem expressed as $P(A/B)=P(B/A) P(A) \div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data 124 into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm 120 may include a gaussian model that follows a normal distribution. Naïve Bayes classification algorithm 120 may include a multinomial model that is used for discrete counts. Naïve Bayes classification algorithm 120 may include a Bernoulli model that may be utilized when vectors are binary.

With continued reference to FIG. 1, computing device 104 may be configured to generate index classifier 112 using a K-nearest neighbors (KNN) algorithm. A "K-nearest neighbors algorithm" as used in this disclosure, includes a classification method that utilizes feature similarity to analyze how closely out-of-sample-features resemble training data 124 to classify input data to one or more clusters and/or categories of features as represented in training data 124; this may be performed by representing both training data 124 and input data in vector forms, and using one or more measures of vector similarity to identify classifications within training data 124, and to determine a classification of input data. K-nearest neighbors algorithm may include specifying a K-value, or a number directing the classifier to select the k most similar entries training data 124 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data 124. Heuristic may include selecting some number of highest-ranking associations and/or training data 124 elements.

Referring again to FIG. 1, computing device 104 is configured to output, from the index classifier 112, a physiologically linked web index. Index classifier 112 may classify biological extraction 108 to a cohort label using a classification algorithm 120 as described above, for instance by identifying a cohort label associated with a cluster of physiological data sets having a greatest degree of similarity to biological extraction 108. In an embodiment, computing device 104 may include additional physiological data associated with user, such as without limitation physiological data received in past biological extractions 108 from user. Physiological data of each user may be stored, without limitation, in a user database 136, which may be implemented using any data structure suitable for implementation of web indices 116 a-n; user database 136 may be located in memory of computing device 104 and/or on another device in and/or in communication with system 100.

With continued reference to FIG. 1, an input 112 relates a representative profile to a nutritional requirement. A "nutritional requirement," as used in this disclosure, is data, including any character, symbolic, and/or numerical data, reflecting the current overall nutritional impact of a meal, snack, and/or drink for a specific group of human profiles and/or representative profiles. A nutritional requirement 128 may be transient and/or dynamic and varies based on ingredients utilized, recipe, cooking instructions, storage impacts, meal size, drink size, snack size, and the like. A nutritional requirement 128 may be graded on a continuum, where a score of zero may indicate a meal, snack, and/or drink which has an extremely poor nutritional impact for a human profile, while a score of 100 may indicate a meal, snack, and/or drink which has an excellent nutritional impact for a human profile. A negative nutritional requirement 128 may reflect a meal, snack, and/or drink that has no beneficial nutritional impact for a human profile and may have a net detrimental impact. In such an instance, a negative nutritional requirement may not contain a numerical assignment.

With continued reference to FIG. 1, computing device 104 is configured to generate a query using an input credential. A "query," as used in this disclosure, is any request generate to retrieve and/or locate information pertaining to an input credential within input database 120. A query may include choosing parameters to generate a query, from a menu of options. For example, computing device 104 may generate a query that contains an entire input credential, a portion of an input credential, a previous input credential, and the like. A query may include query language to locate information pertaining to an input credential. For example, a query may contain language to identify an authority of an input credential, such as to determine if an input credential has been issued by a governing authority such as the INSTITUTE OF MEDICINE, of Washington, District of Columbia. In yet another non-limiting example, a query may include query language to identify information pertaining to an input, such as to determine if an input contains data collected from a randomized control trial or an n-of-1 trial. A query may be generated to locate an input generated by a certain specialist and/or expert authority in the field, such as an input generated by a functional medicine specialist, or an input generated by a neurosurgeon. A query may be generated to locate an input that relates to a particular field and/or specialty, such as an input relating to research in the field of pharmacogenomics or an input relating to information describing new treatments for Parkinson's disease. Computing device 104 authenticates an input credential as a function of a query. Authenticating may include determining that an input credential is valid and has not been revoked or expired. Information pertaining to the status of an input credential may be stored within input database 120. Computing device 104 compares an input credential included with an input, to an input credential stored within input database. Status of input credentials and revocation and/or expiration of input credentials may be updated in real time, utilizing any network methodology as described herein.

With continued reference to FIG. 1, computing device 104 is configured to determine an input credential status as a function of an expert credential list. An "input credential status," as used in this disclosure, is an indication as to the validity and/or veracity of an input credential. An input credential status may reflect if an expert's credentials are currently active, retired, have been revoked, suspended, subject to disciplinary action, subject to a violation, expired, overturned as best practices or best evidence, invalidated, and the like. An input credential status may be stored and maintained within an expert credential list. An input credential status includes a temporal element. A "temporal element," as used in this disclosure, is a timestamp and/or any calendar information, indicating the last time an input credential status was up-dated. For instance and without limitation, a temporal attribute may indicate that an input credential status indicating an expert's credentials are still active, was last validated three days previously. An "expert credential list," as used in this disclosure, is a compilation of a current input credential status of one or more experts. An expert credential list may be stored within input database 120 and updated using any network methodology as described herein. Computing device 104 discards an input as a function of an input credential status. Discarding may include not using an input and marking the input as inactive. Computing device 104 may discard inputs where expert credential list indicates that an input credential status is currently not active, such as if an expert's credentials have been retired, revoked, subject to disciplinary action, subject to a violation, overturned, and the like. Computing device 104 selects a subsequent input including a subsequent input credential. Computing device 104 may select a subsequent input from input database 120.

With continued reference to FIG. 1, computing device 104 is configured to generate a training set using an input. A "training set," as used in this disclosure, is data containing correlation that a machine-learning process may use to model relationships between two or more categories of data elements. For instance, and without limitation, training set 132 may include a plurality of data entries, each entry representing a set of data elements that were recorded, received, and/or generated together; data elements may be correlated by shared existence in a given data entry, by proximity in a given data entry, or the like. Multiple data entries in training set 132 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training set 132 according to various correlations; correlations may indicate causative and/or predictive links between categories of data elements, which may be modeled as relationships such as mathematical relationships by machine-learning processes as described in further detail below. Training set 132 may be formatted and/or organized by categories of data elements, for instance by associating data elements with one or more descriptors corresponding to categories of data elements. As a non-limiting example, training set 132 may include data entered in standardized forms by persons or processes, such that entry of a given data element in a given field in a form may be mapped to one or more descriptors of categories. Elements in training set 132 may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data. Training set 132 may be generated using a classifier, including any of the classifiers as described above in more detail. Training set 132 may be generated using a database, which may utilize an input to retrieve a training set relating to an input from input database. Generating training set 132 includes receiving an input 112 identifying a representative profile 124 from a plurality of representative profiles 124. Computing device 104 identifies a nutritional requirement 128 contained within an identified representative profile 124, and generates training set 132 containing a plurality of nutritional requirements correlated to identified representative profiles 124.

Continuing to refer to FIG. 1, training set 132 may alternatively or additionally include one or more elements that are not categorized; that is, training data may not be formatted or contain descriptors for some elements of data. Machine-learning algorithms and/or other processes may sort training set 132 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training set 132 to be made applicable for two or more distinct machine-learning algorithms as described in further detail below.

With continued reference to FIG. 1, computing device 104 is configured to receive a meal option. A "meal option," as used in this disclosure, is a proposed meal item, including any meal and/or portion of a meal such as but not limited to any breakfast, lunch, dinner, snack, and/or beverage. Information pertaining to a meal option 136 may be stored within input database 120. For example, input database 120 may include information listing one or more meal options that are available for breakfast, such as a first meal option consisting of buckwheat pancakes with maple syrup, a second meal option consisting of a yogurt parfait with granola and fresh berries, and a third meal option consisting of scrambled eggs with toast and bacon. Computing device 104 may select a meal option 136 from a list containing a plurality of meal options 136 within a specified geographical area. Meal options 136 stored within input database 120 may be organized into one or more lists based on meals options 136 that are available within a geographical area. A geographical area may include a global position system (GPS) of a location, including for example, a GPS location of a remote device 116. A geographical area may include a description of the latitude and longitude of a position where a remote device 116 is currently located and/or may be located in the future. A geographical area may be identified using one or more inputs received from remote device 116. For example, computing device 104 may receive a textual input from remote device 116 that specifies a user is located in San Francisco, Calif. In such an instance, computing device 104 identifies meal options 136 available in San Francisco, from a list indicating which meal options 136 are currently available within San Francisco. Information relating to meal options 136 that are available within a geographical area may be contained within one or more lists stored within input database 120. A meal option 136, includes a portion size, indicating what size and/or quantities of a meal option are available. For example, a portion size may indicate that a meal containing chicken alfredo is available in small, medium, large, and extra-large portions. Information relating to available meal options 136 and available portion sizes may be displayed within display interface 108.

With continued reference to FIG. 1, computing device 104 is configured to calculate using a machine learning process a nutritional requirement 128 of a meal option 136 using a training set 132, wherein the machine-learning process uses a meal option 136 and a representative profile 124 as an input, and outputs a nutritional requirement 128. A "machine learning process," as used in this disclosure, is a process that automatically uses a body of data known as "training data" and/or a "training set" to generate an algorithm that will be performed by computing device 104 and/or any module to produce outputs given data provided as inputs; this is in contrast to a non-machine learning software program where the commands to be executed are determined in advance by a user and written in a programming language. A machine-learning process 140 may be implemented, without limitation, as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. A machine-learning process 140 may include generating one or more machine-learning models. A machine learning model includes any mathematical representation of a machine-learning process. A machine learning model may include generating one or more machine-learning algorithms. A machine-learning algorithm may include supervised machine-learning algorithms, unsupervised machine-learning algorithms, lazy learning algorithms, and the like. A machine-learning algorithm utilizes training set 132 to identify patterns in training set 132 so that inputs of a machine-learning algorithm correspond to target outputs of the machine-learning process. A machine-learning algorithm may include one or more machine-learning algorithms, including but not limited to, regression, classification, target, feature, label, overfitting, regularization, parameter and hyper-parameter, and the like.

With continued reference to FIG. 1, computing device 104 determines a nutritional requirement 128 of a meal option 136 as a function of machine-learning process 140. Computing device 104 displays a nutritional requirement 128 within display interface 108. Nutritional requirement 128 includes a range of values. For example, a meal option 136 containing shrimp scampi served on a bed of linguini may contain a nutritional requirement 128 that includes a range of values ranging between 52-75. In such an instance, a range of values may be compared to the standard range, which may be from between 0 to 100, where 0 indicates a meal option that has an unsatisfactory nutritional impact, while a score of 100 indicates a meal option that has a satisfactory nutritional impact. A range of values may aid a user in making informed decisions about a meal option 136, as well as to compare a first meal option 136 to a second meal option 136. For example, a nutritional requirement 128 for a first meal option 136 containing filet mignon with sautéed spinach may contain a first nutritional requirement 128 that ranges between 77-92, while a nutritional requirement 128 for a second meal option 136 containing fried chicken with French fries may contain a second nutritional requirement 128 that ranges between 7-12. In such an instance, a user may compare ranges between a first nutritional requirement 128 and the ranges of a second nutritional requirement 128, to make an informed decision that the first meal option 136 will have an overall more positive impact on a user's health as compared to the second meal option 136.

With continued reference to FIG. 1, computing device 104 receives a user input identifying a food preference. A "food preference," as used in this disclosure, is a label identifying a dietary choice and/or pattern of eating. A food preference may identify particular foods that a user likes and/or dislikes. For example, a food preference may identify that a user likes to consume turkey breast, avocado, mesclun greens, and shrimp, while the user dislikes to consume kale, cauliflower, and Brussel sprouts. A food preference may identify a particular pattern of eating that a user follows, for example, a user who follows a paleo diet or a vegetarian diet. A food preference may identify one or more foods that a user is unable to consume due to an allergy, intolerance, ethical reasons, and/or any other reason that prohibits the user from consuming the food. For example, a food preference may specify that a user does not consume any wheat containing products because the user is intolerant to wheat. Computing device 104 displays a nutritional requirement 128, as a function of a food preference. For example, a food preference that specifies a user follows a ketogenic diet, may be utilized to display a nutritional requirement 128 of a meal option 136 for a user following the ketogenic diet. In yet another non-limiting example, a food preference that specifies a user has an allergy to avocado may be utilized to display a nutritional requirement 128 of a meal option 136 for a user with an allergy to avocado.

Figure 2:
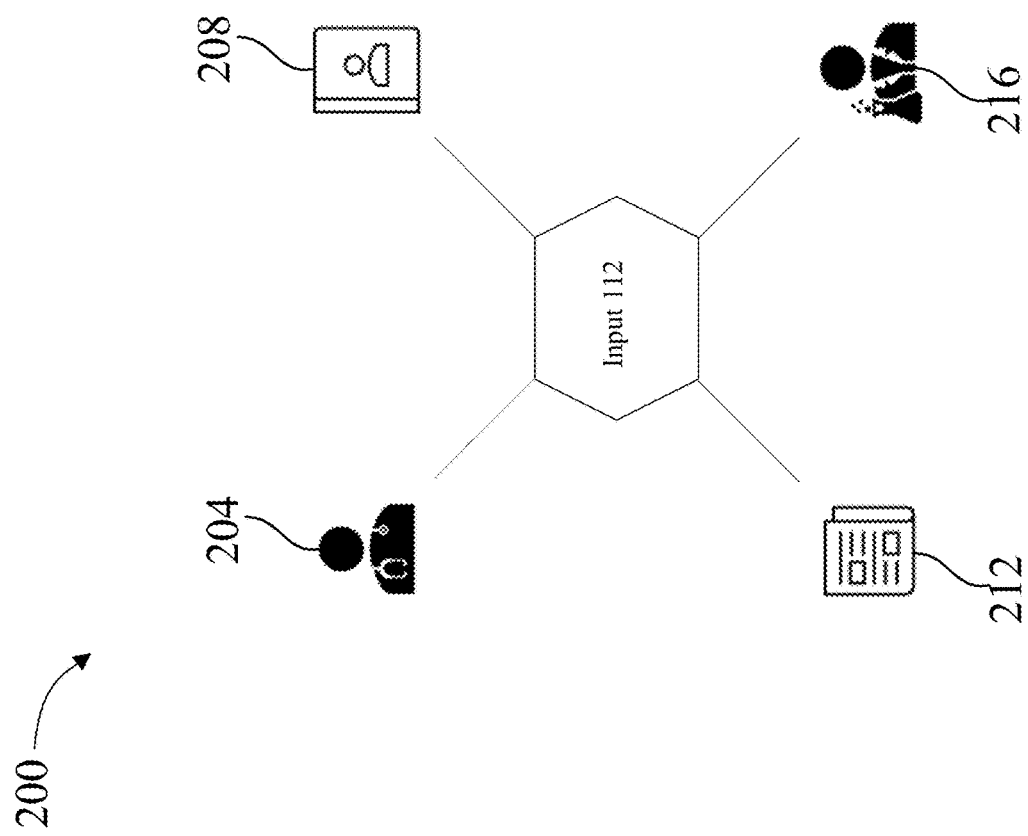
FIG. 2 is a diagrammatic representation of various sources of inputs.

Referring now to FIG. 2, an exemplary embodiment 200 of experts and/or sources of inputs 112 are illustrated. An input 112 relating a representative profile to a nutritional requirement may be generated by an expert clinician 204. An expert clinician 204, may include medical doctors, nutritionists, dieticians, therapist, nurse practitioner, pharmacist, physician assistant, and the like. An input 112 may be generated from expert texts and/or literature 208. Expert texts and/or literature 208 may include books, guidelines, handbooks, encyclopedias, textbooks, magazines, newspapers, and the like. An input 112 may be obtained from primary literature 212. Primary literature 212 may include original research results, journal articles, dissertations, conference proceedings, correspondence, abstracts, indexes, review articles, systemic reviews, meta-analysis, practice guidelines, quantitative research, qualitative research, and the like. An input 112 may be obtained from researchers 216. Researchers 216 may include scientists, academics, professors, mathematicians, medical research scientists, biologists, chemists, and the like.

Figure 3:
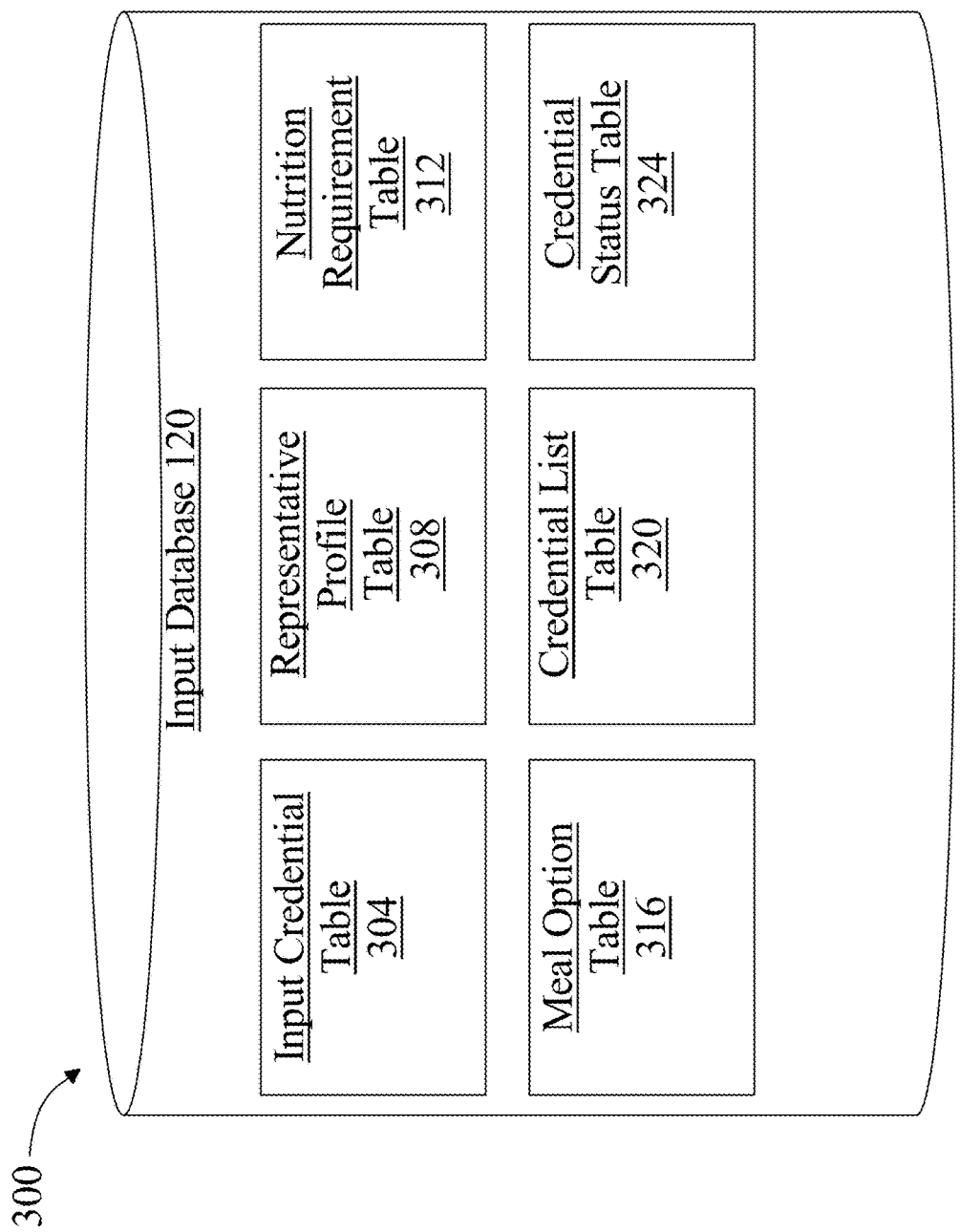
FIG. 3 is a block diagram of an input database.

Referring now to FIG. 3, an exemplary embodiment 300 of input database 120 is illustrated. One or more tables contained within input database 120 may include input credential table 304; input credential table 304 may include information pertaining to one or more input credentials. One or more tables contained within input database 120 may include representative profile table 308; representative profile table 308 may include information pertaining to one or more representative profiles and/or human profiles utilized to create a representative profile. One or more tables contained within input database 120 may include nutritional requirement table 312; nutritional requirement table 312 may include information pertaining to one or more nutritional requirements. One or more tables contained within input database 120 may include meal option table 316; meal option table 316 may include information pertaining to one or more meal options. One or more tables contained within input database 120 may include credential list table 320; credential list table 320 may include information pertaining to one or more credential lists. One or more tables contained within input database 120 may include credential status table 324; credential status table 324 may include information pertaining to the status of one or more credentials.

Figure 4:
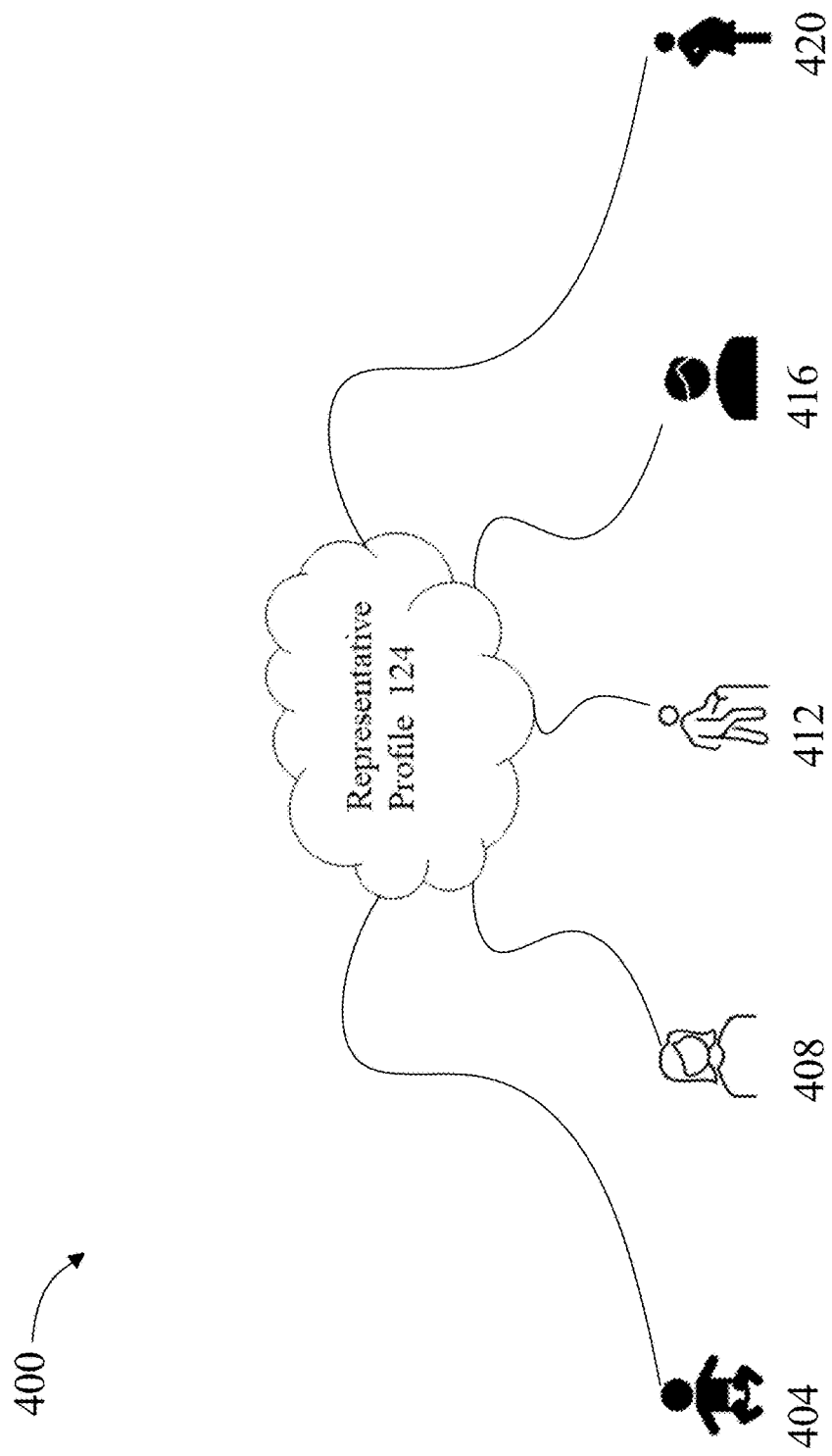
FIG. 4 is a diagrammatic representation of representative profile.

Referring now to FIG. 4, an exemplary embodiment 400 of representative profile 124 is illustrated. Representative profile 124 may be generated using one or more human profiles. A human profile includes any of the human profiles as described above in more detail in reference to FIG. 1. A human profile may include one or more demographic labels. In an embodiment, a representative profile 124 may include a human profile of a toddler 404. In an embodiment, a representative profile 124 may include a human profile of a middle age female 408. In an embodiment, a representative profile 124 may include a human profile of an elderly person 412, who may be age 65 and older. In an embodiment, a representative profile 124 may include a human profile of a middle age male 416. In an embodiment, a representative profile 124 may include a human profile of a pregnant woman 420. Representative profile 124 may be generated using one or more human profiles. For example, representative profile 124 may be generated using human profile of a toddler 408, human profile of a middle age female 408, and human profile of a middle age male 416. Information pertaining to one or more human profiles and/or one or more representative profiles 404 may be stored in input database 120, as described above in more detail.

Figure 5B:
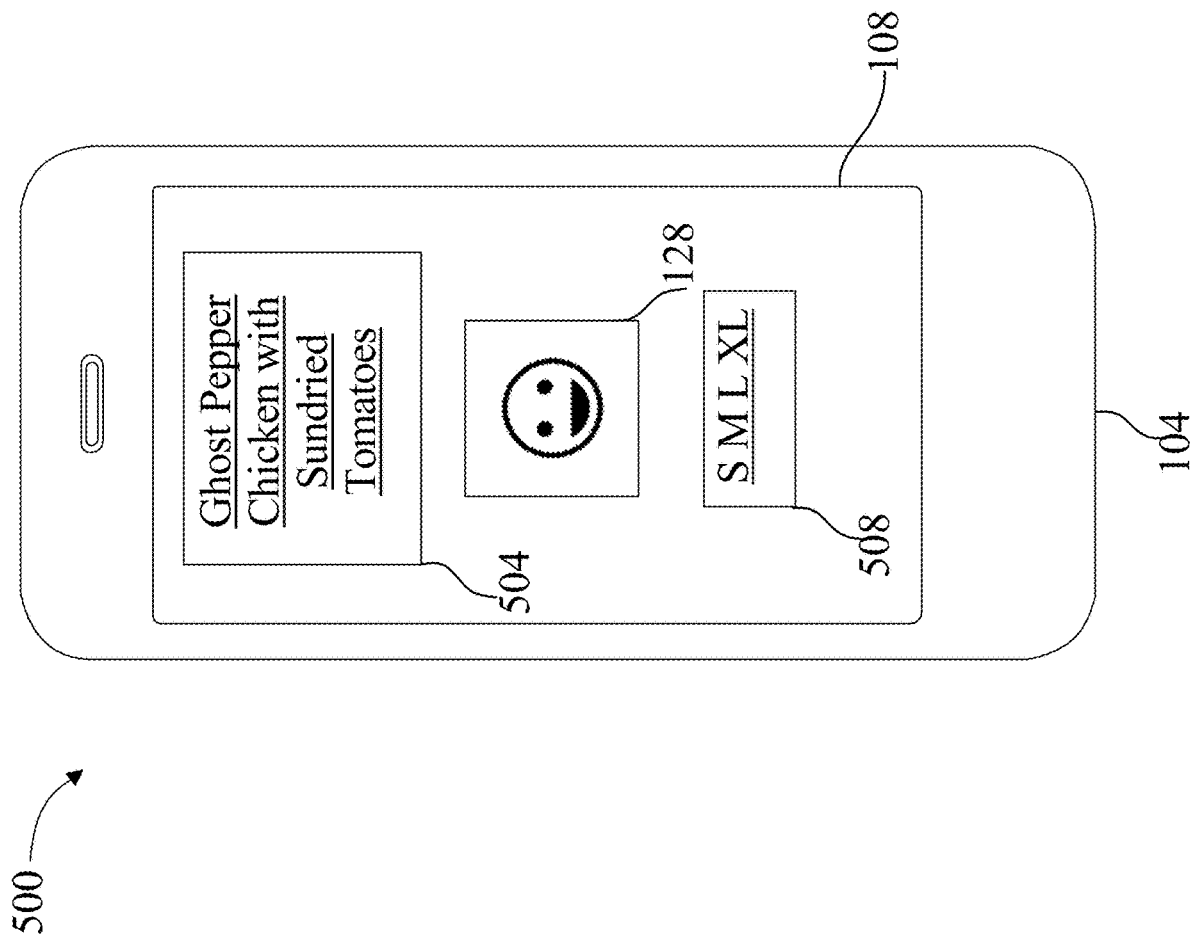

Referring now to FIGS. 5A-5B, an exemplary embodiment 500 of display interface 108 is illustrated. Referring to FIG. 5A, display interface 108 may be displayed within computing device 104. Display interface 108 may display a description 504 of a meal option 136. Display interface 108 may display a nutritional requirement 128 as a numerical score. For example, a meal option 136 containing ghost pepper chicken with sundried tomatoes may have a nutritional requirement 128 containing a numerical score ranging from 41-82. Display interface 108 may include a portion size display 508, where a nutritional requirement 128 may be adjusted based on a selected portion size. In an embodiment, a portion size may range from small, medium, large, and/or extra-large. Referring now to FIG. 5B, display interface 108 may display a nutritional requirement 128 as a character score. For example, a meal option 136 containing ghost pepper chicken with sundried tomatoes may have a nutritional requirement 128 that contains a happy smiley face, indicating the ghost pepper chicken has a positive impact on a user's nutritional state. In such an instance, a nutritional requirement 128 containing a sad face may indicate that a meal option 136 has a negative impact on a user's nutritional state, and a neutral face may indicate a meal option 136 that has neither a positive nor negative impact on a user's nutritional state, but rather a neutral impact.

Figure 6:
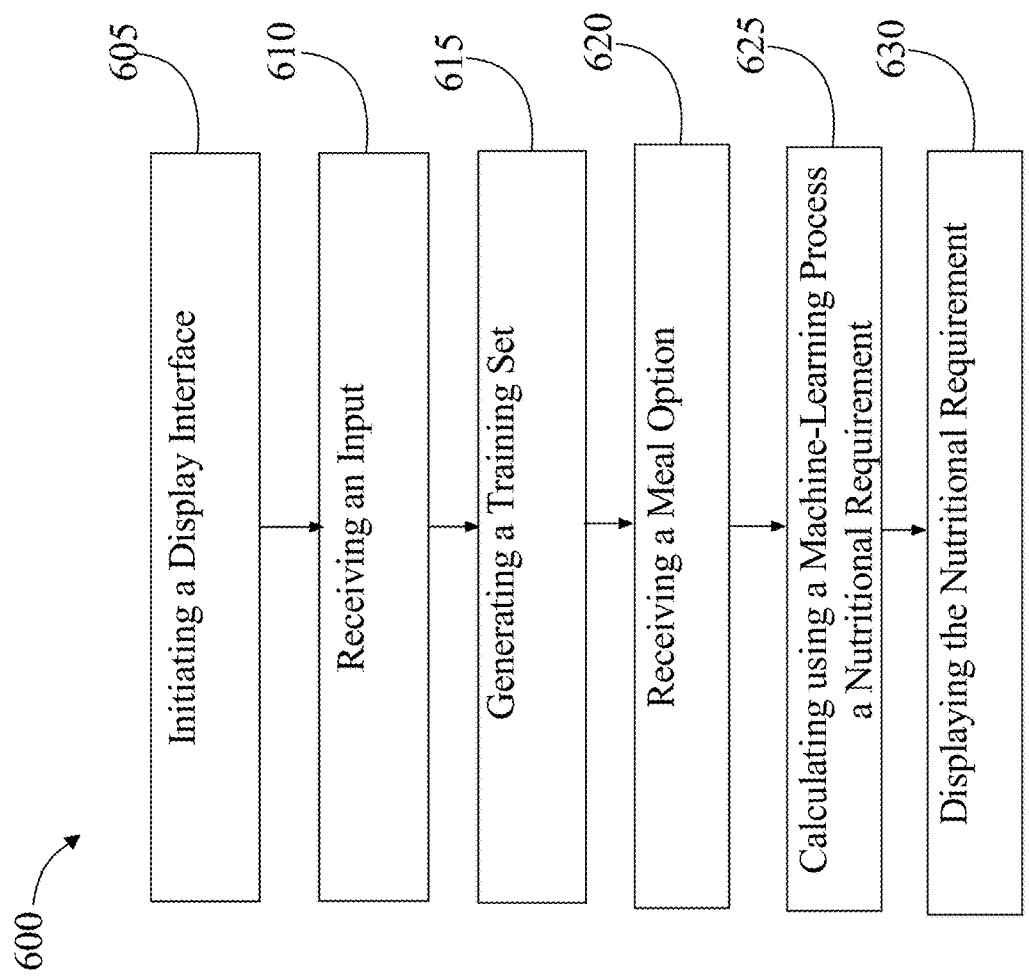
FIG. 6 is a process flow diagram illustrating an exemplary embodiment of a method of calculating nutritional requirements in a display interface.

Referring now to FIG. 6, an exemplary embodiment of a method 600 of calculating nutritional requirements in a display interface is illustrated. At step 605, computing device 104 initiates a display interface 108 within computing device 104. Display interface 108 includes any of the display interfaces 108 as described above in more detail in reference to FIG. 1. Display interface 108 may include graphical icons, text navigation, and/or any other graphical element as described above in more detail in reference to FIG. 1. Display interface 108 may be initiated utilizing any network methodology as described above in more detail in reference to FIG. 1.

With continued reference to FIG. 6, at step 610, computing device 104 retrieves an input 112, including an input credential, and wherein the input 112 relates a representative profile 124 to a nutritional requirement 128. An input 112, includes any of the inputs 112 as described above in more detail in reference to FIG. 1. An input 112 may be received from one or more experts, as described above in more detail in reference to FIGS. 1-2. For instance and without limitation, an input 112 may be received from an expert clinician 204, such as a functional medicine doctor, or a dietician who is considered an expert in the field of holistic nutrition for example. An input 112 may be received from primary literature 212, such as from a journal article published in a medical journal or a thesis containing research published in the field of alternative medicine. An input 112 includes an input credential, identifying any qualification and/or authority that an input 112 contains. For example, an input credential may specify that a user who is a medical doctor is board certified in a medical specialty such as family medicine.

With continued reference to FIG. 6, computing device 104 utilizes an input credential, to authenticate an input 108 as containing good science and good information, and/or to authenticate an input credential, to ensure the qualifications and expert, and/or the source of an input 108. Computing device 104 generates a query using an input credential and authenticates an input credential as a function of the query. A query includes any of the queries as described above in more detail in reference to FIG. 1. A query may include information relating to an input credential and/or part of an input credential. A query may be utilized to locate information contained within input database 120, to determine the accuracy of an input credential. Computing device 104 may compare an input credential to an expert credential list, stored within input database 120. Expert credential list includes any of the expert credential lists as described above in more detail in reference to FIG. 1. Expert credential list includes a list of updated expert credentials. For example, expert credential list may specify if a medical doctor's license to practice medicine has been revoked for disciplinary reasons, or if the contents of a published journal article containing a randomized control trial have been overturned by several other studies. Computing device 104 uses an expert credential list to determine the input credential status. An input credential status may provide an indication as to the validity and/or authenticity of an input 108. An input credential status may contain a temporal element, including any of the temporal elements as described above in more detail in reference to FIG. 1. A temporal element may include a time indicator, specifying when an input credential was last verified and/or updated. Computing device 104 discards an input 108 as a function of an input credential status and selects a subsequent input 108 including a subsequent input credential.

With continued reference to FIG. 1, an input relates a representative profile 124 to a nutritional requirement 128. A representative profile 124, includes any of the representative profiles as described above in more detail in reference to FIGS. 1-5. A representative profile 124 may be generated using one or more human profiles, as described above in more detail in reference to FIGS. 1-5. A representative profile 125 includes a demographic label, including any of the demographic labels as described above in more detail in reference to FIGS. 1-5.

With continued reference to FIG. 6, at step 615, computing device 104 generates a training set 132 using an input 112. Training set 132 includes any of the training sets 132 as described above in more detail in reference to FIG. 1. Training set 132 may be generated utilizing any of the methodologies as described above in more detail in reference to FIG. 1. Generating training set 132 includes receiving an input 112 identifying a representative profile 124 from a plurality of representative profiles 124. Computing device 104 identifies a nutritional requirement 128 contained within an identified representative profile 124, and generates training set 132 containing a plurality of nutritional requirements correlated to identified representative profiles 124.

With continued reference to FIG. 6, at step 620, computing device 104 receives a meal option 136. A meal option 136 includes any of the meal options 136 as described above in more detail in reference to FIG. 1. A meal option 136 includes a proposed meal item. Information pertaining to a meal option 136 may be stored within input database 120. A meal option 136 may include a proposed meal item such as a cheeseburger topped with avocado and served with a side of coleslaw and pickles. A meal option 136 may include a proposed meal item such as a strawberry kiwi flavored kombucha. Computing device 104 receives a meal option 136 from a list containing a plurality of meal options available within a specified geographical area. A geographical area may be determined using any of the techniques as described above in more detail in reference to FIG. 1. For example, a list stored within input database 120 may contain all breakfast, lunch, dinner, and beverage items available within downtown San Francisco. A meal option 136 identifies a portion size, including any of the portion sizes as described above in more detail in reference to FIGS. 1-5.

With continued reference to FIG. 6, at step 625, computing device 104 calculates using a machine learning process 140, a nutritional requirement 128 of a meal option 136 using training set 132. A machine learning process 140, includes any of the machine learning processes as described above in more detail in reference to FIG. 1. A machine-learning process 140 may be implemented using any of the methodologies as described above in more detail in reference to FIG. 1. Generating machine-learning process 140 includes utilizing a representative profile 124 and a meal option 136 as an input and outputting a nutritional requirement 128. Machine learning process 140 may be implemented as a supervised machine leaning process, or a lazy learning process as described above in more detail in reference to FIG. 1.

With continued reference to FIG. 6, computing device 104 determines a nutritional requirement 128 of a meal option as a function of calculating a machine-learning process 140. A nutritional requirement 128 may contain an indication as to the current overall nutritional impact of a meal, snack, and/or drink for a specific group of human profiles. A nutritional requirement 128 may include a numerical score, such as a range as described above in more detail in reference to FIGS. 1-5. A nutritional requirement 128 may include a character score, as described above in more detail in reference to FIGS. 1-5. A nutritional requirement 128 may aid a user in making an informed decision regarding a meal option 136.

With continued reference to FIG. 6, at step 630, computing device 104 displays a nutritional requirement 128 within display interface 108. In an embodiment, computing device 104 may transmit and display interface 108 within remote device 116. Computing device 104 may display a nutritional requirement 128 as a numerical output including a range of values. For example, a nutritional requirement 128 for a meal option 136 including filet mignon with mushrooms and gravy may be displayed as a numerical output including a range between 72-84. A numerical output may provide context to a user and aid a user in selecting a meal option 136. Computing device 104 receives a user input identifying a food preference. A user input includes any of the user inputs as described above in more detail in reference to FIG. 1. A user input may include a description of a diet that a user may be following, or a particular style of eating. Computing device 104 displays a nutritional requirement 128 as a function of a food preference. For example, a user input may specify that a user follows a paleo diet. In such an instance, computing device 104 displays a nutritional requirement 128 of a meal option 136 for a paleo diet.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
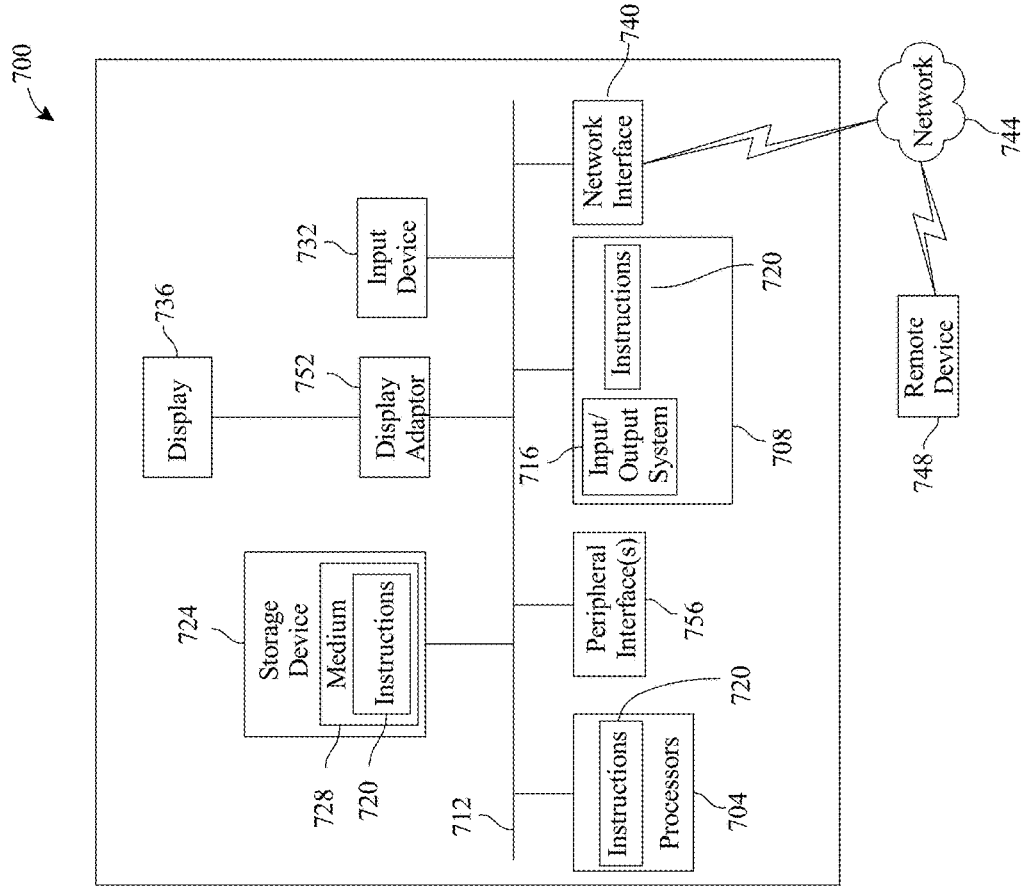
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Memory 708 may include various components (e.g., machine-readable media) including, but not limited to, a random access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for calculating nutritional requirements in a display interface, the system comprising a computing device, the computing device configured to:
   initiate, a display interface within the computing device;
   retrieve, an input from an expert, wherein the input comprises an input credential, wherein the input credential is an entry identifying qualifications of the expert that created the input;
   generate an index classifier, wherein the index classifier comprises a machine-learning model trained by training data comprising a plurality of user physiological data records and a plurality of user cohort labels configured to receive biological extractions as inputs and outputs web search indices, the index classifier further comprising a classification algorithm clustering a plurality of user physiological data records to a plurality of user cohort labels;
   search, by the web index classifier, wherein a result of the search further comprise at least a classifier wherein the classifier is trained using an index training data set comprising the results of the search wherein the results of the search further comprises the plurality of user cohort labels, wherein the classifier is further configured to:
      receive at least the result of the search;
      correlate the at least result of the search to at least an element of physiological data to the plurality of user cohort labels;
      and classify the plurality of user cohort labels to a representative profile as a function of the results of the search;
   select a representative profile as a function of the classifier, wherein selecting further comprises:
      classifying the user to a selected user cohort label of the plurality of user cohort labels; and
      selecting the representative profile as a function of the selected user cohort label;
   receive, by a computing device, a user input, wherein the computing device is further configured to identify a food preference as a function of the user input wherein the food preference is further configured to specify the user's allergies, wherein identifying the food preference further comprises:
      identifying a pattern of eating of the user as a function of the food preference; and
      displaying a nutritional requirement as a function of the food preference;
   classify the representative profile to the nutritional requirement as a function of the input;
   generate, a training set using the input, wherein generating the training set further comprises:
      receiving the input identifying the representative profile from a plurality of representative profiles;
      identifying a nutritional requirement contained within the identified representative profile; and
      generating the training set wherein the training set contains a plurality of nutritional requirements correlated to the identified representative profile;
   receive a meal option;
   display a description of the meal option in the display interface;
   calculate the nutritional requirement of the meal option, wherein calculating comprises:
      training a machine-learning process as a function of the training set, wherein training the machine-learning process comprises determining a plurality of distances associated with the plurality of nutritional requirements as a function of correlations between the plurality of nutritional requirements and the identified representative profile; and
      calculating the nutritional requirement, wherein the machine learning model inputs the representative profile and the meal option and outputs the nutritional requirement according the plurality of distances associated with the plurality of nutritional requirements; and
   display a graphical representation of the nutritional requirement from a group of two or more graphical representations within the display interface with the description of the meal option as a function of the calculated nutritional requirement, wherein the graphical representation of the nutritional requirement comprises at least a character score.

2. The system of claim 1, wherein the representative profile further comprises a demographic label.

3. The system of claim 1, wherein the computing device is further configured to:
   generate a query using the input credential; and
   authenticate the input credential as a function of the query, wherein the authentication comprises determining that an input credential is valid and has not been revoked or has not expired.

4. The system of claim 1, wherein the computing device is further configured to:

determine an input credential status as a function of an expert credential list;

discard the input as a function of the input credential status; and select a subsequent input including a subsequent input credential.

5. The system of claim 4, wherein the input credential status contains a temporal element.

6. The system of claim 1, wherein the meal option is selected from a list containing a plurality of meal options within a specified geographical area.

7. The system of claim 1, wherein the computing device is further configured to:

receive a portion size associated with the meal option; and update the graphical representation of the nutritional requirement to another from the group of two or more graphical representations based on the portion size.

8. The system of claim 1, wherein identifying the food preference further specifies at least a food that the user cannot consume due to at least an intolerance.

9. The system of claim 1, wherein the nutritional requirement is displayed as a numerical output including a range of values.

10. The system of claim 1, wherein the computing device is further configured to generate the plurality of user cohort labels using a feature learning algorithm.

11. A method of calculating nutritional requirements in a display interface the method comprising:

initiating by a computing device, a display interface within the computing device;

retrieving by the computing device, an input from an expert, wherein the input comprises an input credential, wherein the input credential is an entry identifying a qualification of the expert that created the input;

generating, by the computing device, an index classifier, wherein the index classifier comprises a machine-learning model trained by training data comprising a plurality of user physiological data records and a plurality of user cohort labels configured to receive biological extractions as inputs and outputs web search indices, the index classifier further comprising a classification algorithm clustering a plurality of user physiological data records to a plurality of user cohort labels;

searching, by the web index classifier, wherein a result of the search further comprise at least a classifier wherein the classifier is trained using an index training data set comprising the results of the search wherein the results of the search further comprises the plurality of user cohort labels, wherein the classifier is further configured to:

receive at least the result of the search;

correlate the at least result of the search to at least an element of physiological data to the plurality of user cohort labels;

and classify the plurality of user cohort labels to a representative profile as a function of the results of the search;

selecting by computing device, a representative profile as a function of the classifier, wherein selecting further comprises:

classifying the user to a selected user cohort label of the plurality of user cohort labels; and selecting the representative profile as a function of the selected user cohort label;

receiving, by a computing device, a user input, wherein the computing device is further configured to identify a food preference as a function of the user input wherein the food preference is further configured to specify the user's allergies, wherein identifying the food preference further comprises:

identifying a pattern of eating of the user as a function of the food preference; and displaying a nutritional requirement as a function of the food preference;

classifying, by the computing device, the representative profile to the nutritional requirement as a function of the input;

generating by the computing device, a training set using the input, wherein generating the training set further comprises:

receiving the input identifying the representative profile from a plurality of representative profiles;

identifying a nutritional requirement contained within the identified representative profile; and generating the training set wherein the training set contains a plurality of nutritional requirements correlated to the identified representative profile;

receiving by the computing device, a meal option;

displaying, in the display interface, a description of the meal option in the display interface;

calculating by the computing device, the nutritional requirement of the meal option, wherein calculating comprises training a machine-learning process as a function of the training set, wherein training the machine-learning process comprises determining a plurality of distances associated with the plurality of nutritional requirements as a function of correlations between the plurality of nutritional requirements and the identified representative profile and wherein the machine-learning process inputs the nutritional requirement and the meal option and outputs the nutritional requirement according the plurality of distances associated with the plurality of nutritional requirements; and displaying by the computing device, a graphical representation of the nutritional requirement from a group of two or more graphical representations within the display interface with the description of the meal option as a function of the calculated nutritional requirement, wherein the graphical representation of the nutritional requirement comprises at least a character score.

12. The method of claim 11, wherein the representative profile further comprises a demographic label.

13. The method of claim 11, wherein retrieving the input further comprises:

generating a query using the input credential; and authenticating the input credential as a function of the query, wherein authenticating comprises determining that the input credential is valid and has not been revoked or has not expired.

14. The method of claim 11, wherein retrieving the input further comprises:

determining the input credential status as a function of an expert credential list;

discarding the input as a function of the input credential status; and selecting a subsequent input including a subsequent input credential.

15. The method of claim 14, wherein the input credential status contains a temporal element.

16. The method of claim 11, wherein the meal option is selected from a list containing a plurality of meal options within a specified geographical area.

17. The method of claim 11, further comprising:
receiving a portion size associated with the meal option; and
updating the graphical representation of the nutritional requirement to another from the group of two or more graphical representations based on the portion size.

18. The method of claim 11, wherein displaying the nutritional wherein identifying the food preference further specifies at least a food that the user cannot consume due to at least an intolerance.

19. The method of claim 11, wherein the nutritional requirement is displayed as a numerical output including a range of values.

20. The method of claim 11 further comprising generating the plurality of user cohort labels using a feature learning algorithm.

\* \* \* \* \*